United States Patent
Ludviksson et al.

(10) Patent No.: US 6,894,769 B2
(45) Date of Patent: May 17, 2005

(54) MONITORING EROSION OF SYSTEM COMPONENTS BY OPTICAL EMISSION

(75) Inventors: Audunn Ludviksson, Scottsdale, AZ (US); Eric J. Strang, Chandler, AZ (US)

(73) Assignee: Tokyo Electron Limited, Tokyo (JP)

( * ) Notice: Subject to any disclaimer, the term of this patent is extended or adjusted under 35 U.S.C. 154(b) by 129 days.

(21) Appl. No.: 10/331,456

(22) Filed: Dec. 31, 2002

(65) Prior Publication Data

US 2004/0125360 A1 Jul. 1, 2004

(51) Int. Cl.[7] .............................. G01J 3/30; G01N 21/64
(52) U.S. Cl. ....................... 356/72; 356/316; 250/459.1
(58) Field of Search ...................... 356/72–73, 316–317, 356/311; 250/458.1–461.1

(56) References Cited

U.S. PATENT DOCUMENTS

| | | | | |
|---|---|---|---|---|
| 5,146,098 A | * | 9/1992 | Stack | ....................... 250/492.2 |
| 5,187,542 A | * | 2/1993 | Madzsar | ...................... 356/311 |
| 5,712,702 A | * | 1/1998 | McGahay et al. | ........... 356/311 |
| 5,798,016 A | * | 8/1998 | Oehrlein et al. | ............. 156/914 |
| 5,947,053 A | * | 9/1999 | Burnham et al. | ......... 250/492.2 |
| 6,077,387 A | | 6/2000 | Tesauro | |
| 6,153,123 A | | 11/2000 | Hampden-Smith et al. | |
| 2002/0149001 A1 | * | 10/2002 | Ellens et al. | ........... 252/301.4 S |

* cited by examiner

*Primary Examiner*—Zandra Smith
*Assistant Examiner*—Kara Geisel
(74) *Attorney, Agent, or Firm*—Oblon, Spivak, McClelland, Maier & Neustadt, P.C.

(57) ABSTRACT

A method and system are provided for monitoring erosion of system components in a plasma processing system. The system components contain emitters that are capable of producing characteristic fluorescent light emission when exposed to a plasma. The method utilizes optical emission to monitor fluorescent light emission from the emitters for determining system component status. The method can evaluate erosion of system components in a plasma, by monitoring fluorescent light emission from the emitters. Consumable system components that can be monitored using the method include rings, shields, electrodes, baffles, and liners.

43 Claims, 14 Drawing Sheets

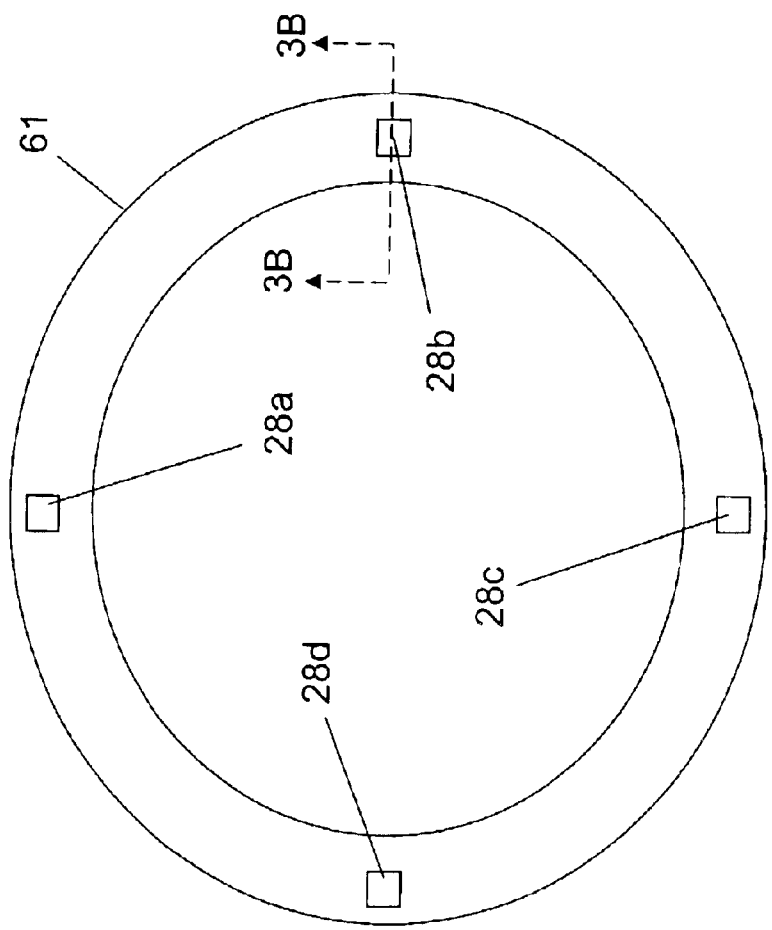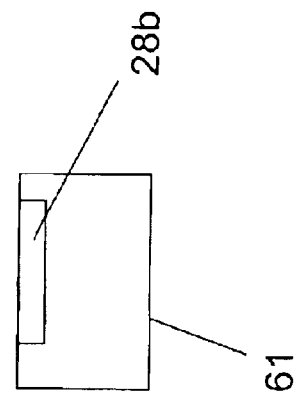
FIG. 3A
FIG. 3B

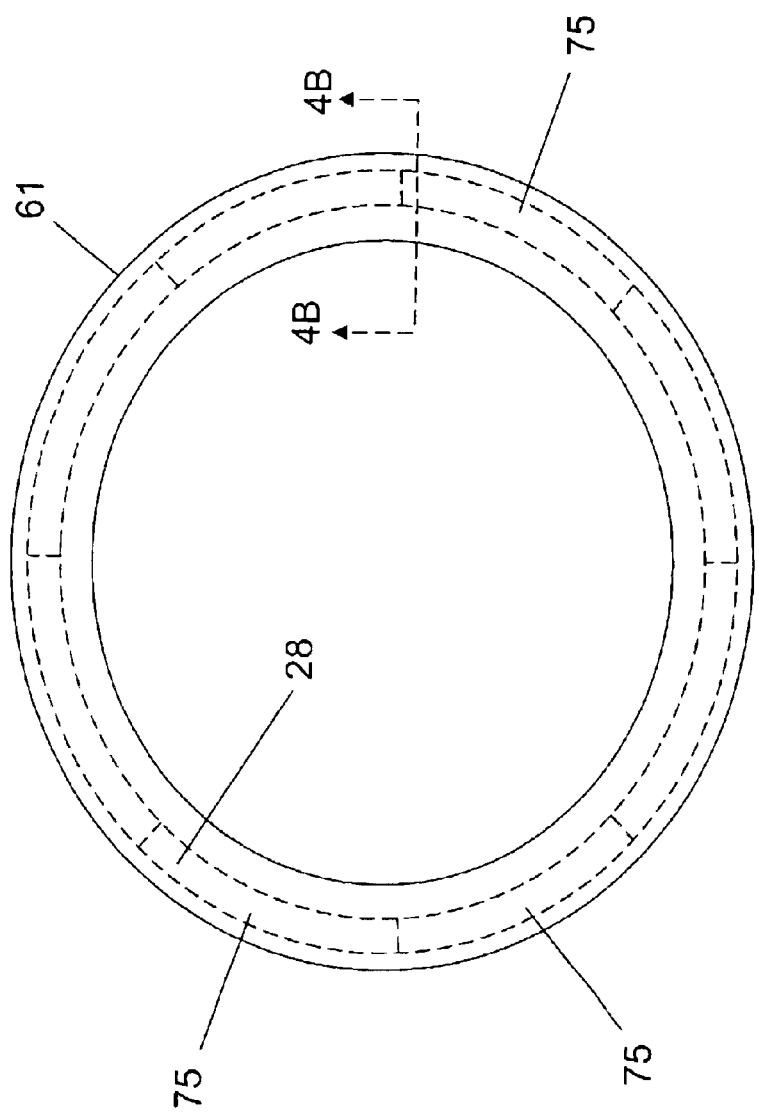
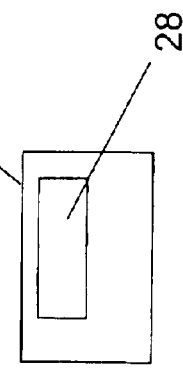
FIG. 4A
FIG. 4B

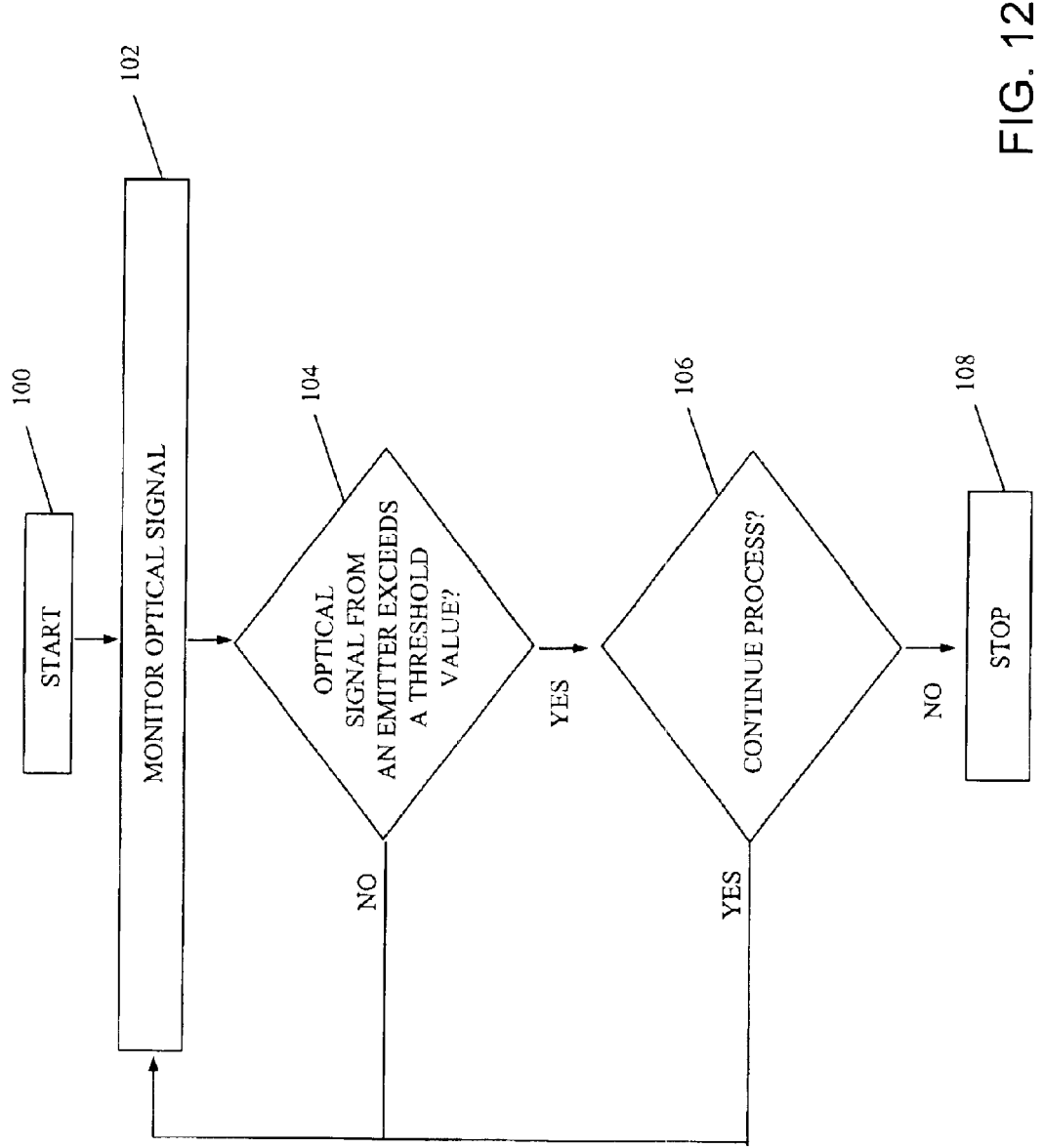

MONITORING EROSION OF SYSTEM COMPONENTS BY OPTICAL EMISSION

CROSS REFERENCE TO RELATED APPLICATIONS

The present invention is related to U.S. patent application Ser. No. 10/331,349, filed on Dec. 31, 2002, the entire contents of which are herein incorporated by reference.

FIELD OF THE INVENTION

The present invention relates to plasma processing and more particularly to monitoring the erosion of system components in a plasma processing system using an optical monitoring system.

BACKGROUND OF THE INVENTION

The fabrication of integrated circuits (IC) in the semiconductor industry typically employs plasma to create and assist surface chemistry within a plasma reactor necessary to remove material from and deposit material to a substrate. In general, plasma is formed within the plasma reactor under vacuum conditions by heating electrons to energies sufficient to sustain ionizing collisions with a supplied process gas. Moreover, the heated electrons can have energy sufficient to sustain dissociative collisions and, therefore, a specific set of gases under predetermined conditions (e.g., chamber pressure, gas flow rate, etc.) are chosen to produce a population of charged species and chemically reactive species suitable to the particular process being performed within the chamber (e.g., etching processes where materials are removed from the substrate or deposition processes where materials are added to the substrate).

Although the formation of a population of charged species (ions, etc.) and chemically reactive species is necessary for performing the function of the plasma processing system (i.e. material etch, material deposition, etc.) at the substrate surface, other component surfaces on the interior of the processing chamber are exposed to the physically and chemically active plasma and, in time, can erode or become coated with deposits. The erosion or coating of exposed system components in the plasma processing system can lead to a gradual degradation of the plasma processing performance and ultimately to complete failure of the system.

Various parts of a plasma processing system consist of consumable or replaceable components, that are fabricated from silicon, quartz, alumina, carbon, or silicon carbide, for example. Examples of consumable system components include electrodes, shields, rings, baffles, and liners. The consumable nature of the replaceable components can require frequent maintenance of the plasma processing system. This frequent maintenance can produce costs associated with plasma processing down-time and new plasma processing chamber components, which can be excessive.

Consumable parts are commonly replaced after detrimental processing conditions or processing results are observed. These adverse processing conditions can include plasma arcing, particle formation, variations in substrate etch rate, etch selectivity, and etch uniformity. Alternatively, consumable parts can be cleaned or replaced according to a predetermined maintenance schedule that can, for example, be based on the number of plasma operating hours. These methods can result in overdue or premature replacement of consumable system components.

SUMMARY OF THE INVENTION

A plasma processing system is provided that allows for monitoring erosion of system components during plasma processing. The plasma processing system comprises a processing chamber and an optical monitoring system for monitoring light emission from the processing chamber. System components are provided that can contain at least one emitter that is capable of fluorescent light emission when exposed to a plasma.

A method is provided for monitoring the erosion of system components in a plasma processing system. The system components can contain at least one emitter that can produce characteristic fluorescent light emission when exposed to a plasma. The method utilizes an optical monitoring system to monitor the fluorescent light emission.

Monitorable consumable system components are provided that can contain at least one emitter that can produce characteristic fluorescent light emission when exposed to a plasma. The emitters allow for monitoring erosion of the consumable system components.

BRIEF DESCRIPTION OF THE DRAWINGS

The accompanying drawings, which are incorporated in and constitute a part of the specification, embodiments of the invention, and together with the general description given above and the detailed description of the embodiments given below, serve to explain the principles of the invention wherein:

FIG. 3A shows a plan view of a system component containing a plurality of emitters;

FIG. 3B shows a cross-sectional view of the system component in FIG. 3A;

FIG. 4A shows a plan view of a system component containing an emitter;

FIG. 4B shows a cross-sectional view of the system component in FIG. 4A;

FIG. 12 is a flowchart for monitoring the status of system components using optical emission.

DETAILED DESCRIPTION OF THE INVENTION

Figure 1:
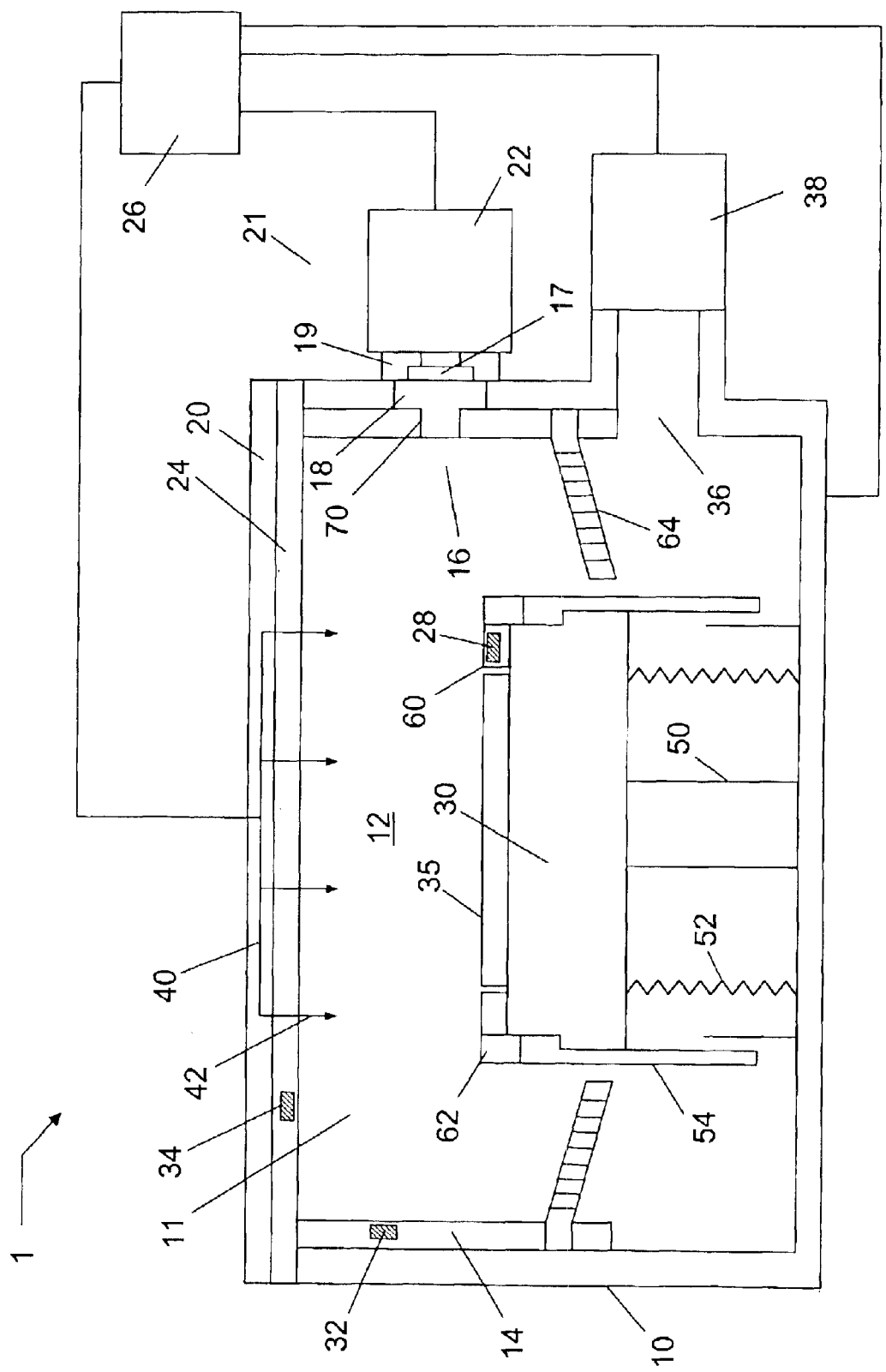
FIG. 1 shows a simplified block diagram of a plasma processing system.

FIG. 1 shows a simplified block diagram of a plasma processing system. A plasma processing system 1 is depicted in FIG. 1 comprising a plasma processing chamber 10, an upper assembly 20, an electrode plate 24, a substrate holder 30 for supporting a substrate 35, and a pumping duct 36 coupled to a vacuum pump 38 for providing a reduced pressure atmosphere 11 in plasma processing chamber 10. Plasma processing chamber 10 can facilitate the formation of a processing plasma in a process space 12 adjacent substrate 35. The plasma processing system 1 can be configured to process various substrates (i.e. 200 mm substrates, 300 mm substrates, or larger).

A gas injection assembly 40 can introduce process gas 42 to the plasma processing chamber 10. The gas injection system 40 can include a showerhead, wherein the process gas 42 is supplied from a gas delivery system (not shown) to the process space 12 through a gas injection plenum (not shown), a series of baffle plates (not shown) and a multi-orifice showerhead gas injection plate (not shown).

For example, an electrode plate 24 can be coupled to an RF source (not shown), and facilitate an upper electrode for the plasma processing system 1. In an alternate embodiment, the upper assembly 20 comprises a cover and an electrode plate 24, wherein the electrode plate 24 is maintained at an electrical potential equivalent to that of the plasma processing chamber 10. For example, the plasma processing chamber 10, the upper assembly 20, and the electrode plate 24 can be electrically connected to ground potential, and facilitate an upper electrode for the plasma processing system 1.

Plasma processing chamber 10 can, for example, further comprise a shield 14 and chamber liners (not shown) for protecting the plasma processing chamber 10 from the processing plasma in the process space 12, and an optical viewport 16. Optical viewport 16 can comprise an optical window 17 coupled to the backside of an optical window deposition shield 18, and an optical window flange 19 can be configured to couple optical window 17 to the optical window deposition shield 18. Sealing members, such as O-rings, can be provided between the optical window flange 19 and the optical window 17, between the optical window 17 and the optical window deposition shield 18, and between the optical window deposition shield 18 and the plasma processing chamber 10. Optical window deposition shield 18 can extend through an opening 70 within shield 14. Optical monitoring system 21 can permit monitoring of optical emission from the processing plasma in process space 12 using optical viewport 16 and optical diagnostic sensor 22.

A spectrometer (not shown) can be incorporated in the optical diagnostic sensor 22 to detect a plasma process condition based on an optical emission, e.g., light, from the process space 12. The spectrometer or the detector system can be associated with a photomultiplier tube, a CCD or other solid state detector to at least partially detect a plasma process condition, such as an endpoint of a plasma process, or status of a system component, for example. However, other optical devices capable of analyzing optical emission, can be used as well.

Substrate holder 30 can, for example, further comprise a vertical translational device 50 surrounded by a bellows 52 coupled to the substrate holder 30 and the plasma processing chamber 10, and configured to seal the vertical translational device 50 from the reduced pressure atmosphere 11 in plasma processing chamber 10. Additionally, a bellows shield 54 can, for example, be coupled to the substrate holder 30 and configured to protect the bellows 52 from the processing plasma. Substrate holder 30 can, for example, further be coupled to at least one of a focus ring 60, and a shield ring 62. Furthermore, a baffle plate 64 can extend about a periphery of the substrate holder 30.

Substrate 35 can be transferred into and out of plasma processing chamber 10 through a slot valve (not shown) and chamber feed-through (not shown) via robotic substrate transfer system where it is received by substrate lift pins (not shown) housed within substrate holder 30 and mechanically translated by devices housed therein. Once substrate 35 is received from substrate transfer system, it is lowered to an upper surface of substrate holder 30.

Substrate 35 can be affixed to the substrate holder 30 via an electrostatic clamping system. Furthermore, substrate holder 30 can, for example, further include a cooling system including a re-circulating coolant flow that receives heat from substrate holder 30 and transfers heat to a heat exchanger system (not shown), or when heating, transfers heat from the heat exchanger system. Moreover, gas can, for example, be delivered to the backside of substrate 35 via a backside gas system to improve the gas-gap thermal conductance between substrate 35 and substrate holder 30. Such a system can be utilized when temperature control of the substrate is required at elevated or reduced temperatures. In other embodiments, heating elements, such as resistive heating elements, or thermoelectric heaters/coolers can be included.

In FIG. 1, substrate holder 30 can comprise an electrode through which RF power is coupled to the processing plasma in process space 12. For example, substrate holder 30 can be electrically biased at a RF voltage via the transmission of RF power from a RF generator (not shown) through an impedance match network (not shown) to substrate holder 30. The RF bias can serve to heat electrons to form and maintain plasma. In this configuration, the system can operate as a reactive ion etch (RIE) reactor, wherein the chamber and upper gas injection electrode serve as ground surfaces. A typical frequency for the RF bias can range from 1 MHz to 100 MHz. For example, plasma processing systems operating at 13.56 MHz are well known to those skilled in the art.

The processing plasma formed in process space 12 can be formed using a plasma source configured to create a plasma from a process. The plasma source can include a parallelplate, capacitively coupled plasma (CCP) source, an inductively coupled plasma (ICP) source, any combination thereof, and with and without DC magnet systems. Alternately, the processing plasma in process space 12 can be formed using electron cyclotron resonance (ECR). In yet another embodiment, the processing plasma in process space 12 is formed from the launching of a Helicon wave. In yet another embodiment, the processing plasma in process space 12 is formed from a propagating surface wave.

A controller 26 includes a microprocessor, a memory, and a digital I/O port capable of generating control voltages sufficient to communicate and activate inputs to the processing system 1 as well as monitor outputs from the processing system 1. Moreover, the controller 26 is coupled to and can exchange information with the plasma processing chamber 10, the gas injection system 40, optical diagnostic sensor 22, and the vacuum pump system 38. For example, a program stored in the memory can be utilized to control the aforementioned components of a plasma processing system 1 according to a stored process recipe. One example of controller 26 is a DELL PRECISION WORKSTATION 610™, available from Dell Corporation, Dallas, Tex.

Various system components can contain emitters that are capable of producing characteristic fluorescent light emission to indicate component status in the presence of a plasma. The system components can include, but are not limited to, focus ring 60 containing emitter 28, shield 14 containing emitter 32, and electrode plate 24 containing emitter 34. These exemplary system components are consumable parts that commonly erode during plasma processing, and therefore require status monitoring to facilitate proper replacing.

The role of focus ring 60 that encircles the substrate 35, includes control of the substrate etch rate, etch selectivity, and etch uniformity on the periphery of the substrate 35. The extent of plasma erosion of focus ring 60 is commonly determined ex-situ by removing the focus ring 60 from the plasma processing system 1 and measuring the reduction in the thickness of the focus ring 60. For example, erosion of the order of few tenths of a mm in the thickness of the focus ring 60, can require replacement of the eroded focus ring 60.

During manufacturing of various system components, emitters may be integrated into the system component structures to allow monitoring of component status. The integration of emitters into system components can be designed so that the emitters become exposed to the plasma environment when the system components need to be replaced. The preferred location (depth) of the emitters in the system components can be determined from process history and process requirements.

Various consumable or replaceable components of a plasma processing system are, for example, fabricated from silicon, quartz, alumina, carbon, or silicon carbide. Examples of consumable system components that are fabricated from these materials include electrodes, shields, rings, baffles, and liners. The consumable nature of the replaceable components can require frequent maintenance of the plasma processing system. In addition to the above-mentioned materials, system components (e.g., deposition shields) can be fabricated from metals (e.g., aluminum) and metal alloys (e.g., stainless steel) and require frequent cleaning or replacing.

Various materials (e.g., quartz and alumina) that are used to manufacture system components are substantially transparent to plasma light over a wide range of wavelengths. Fluorescent emission can be observed from emitters in these materials, even though the emitters are not in direct contact with the plasma environment. Direct exposure of the emitters to the plasma can, for example, be determined when the fluorescent light emission exceeds a threshold value.

Monitoring system component status using an optical monitoring system can include determining if the intensity level of the fluorescent emission associated with a system component exceeds a threshold value, arriving at a determination of whether the system component needs to be replaced, and based on the determination, either continuing with the process or stopping the process.

When the emitters are excited by a plasma, plasma light is absorbed and subsequently re-emitted as fluorescent light, that is shifted to longer wavelengths than the absorbed plasma light. The absorbed plasma light can, for example, be in the UV region and the emitted fluorescent light can be in the visible region. The shift to longer wavelengths can be advantageous, since light in the visible region is less affected by contaminants, such as polymers and by-products, that can deposit on the optical window 17 of the optical monitoring system 21 during processing. Exposure of the emitters to energetic species, other than light, in the plasma (e.g., excited gas species), can also result in fluorescent light emission.

The emitters can be selected from a wide variety of fluorescent materials, that are commercially available in the form of rigid or non-rigid sheets, fine powders, or paints, for example. The emitters can contain at least one material having fluorescent properties corresponding to a light wavelength produced in a plasma. The fluorescent materials can be selected in view of the desired fluorescent properties, that can depend on the plasma species, and the plasma chemistry. The selection of a fluorescent material may be evaluated in view of possible contamination of the process environment, due to exposure of the fluorescent material to the plasma, and possible erosion of fluorescent material from system components.

Phosphors compounds are examples of fluorescent materials that are frequently used in display applications. Phosphors are capable of emitting light in the visible and/or ultraviolet spectrums upon excitation of the material by an external energy source such as a plasma. Phosphor powders can have well-controlled color characteristics, sometimes referred to as emission spectrum characteristics or chromaticity. Phosphors typically include a matrix compound, referred to as a host material, and one or more dopants, referred to as activator ions, to emit a specific color or to enhance the luminescence characteristics. The phosphor materials (the color of the fluorescent light in parentheses), can include $Y_2O_3$:Eu (red), $Y_2O_2S$:Eu, Tb or combinations thereof (red), thiogallates (e.g., $SrGa_2S_4$:Eu (green)), ZnS:Cu, Al or combinations thereof (green), $SrGa_2S_4$:Ce (blue), ZnS:Ag, Au or Cl or combinations thereof (blue), and $SrGa_2S_4$:Ce (blue). The above-identified phosphors are exemplary; a wide variety of other phosphors can be utilized.

Figure 2A:
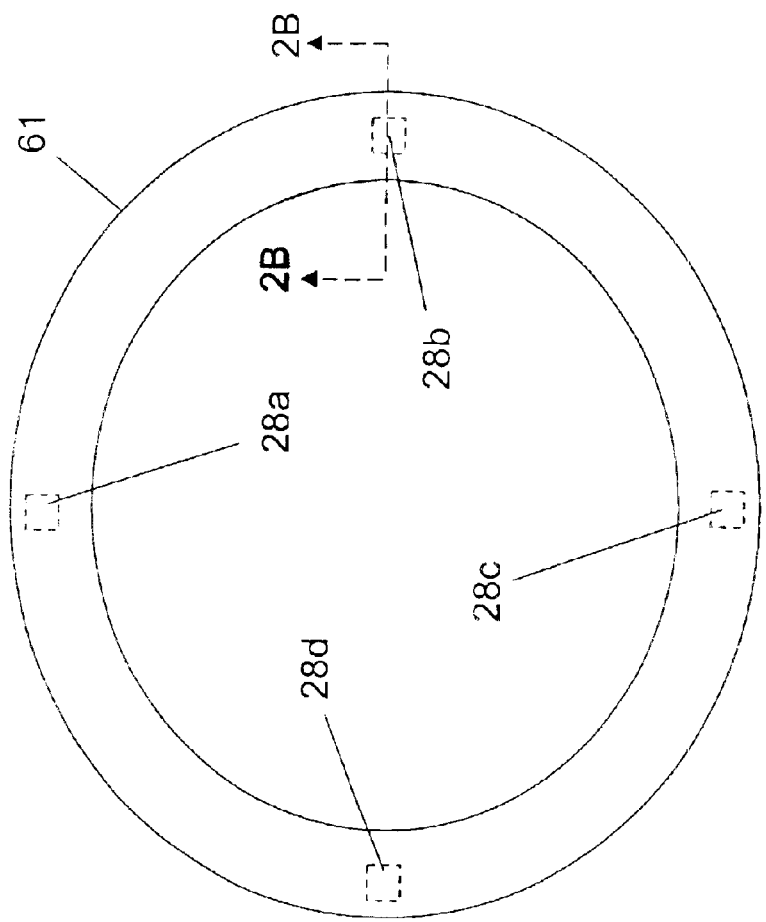
FIG. 2A shows a plan view of a system component containing a plurality of emitters.
Figure 2B:
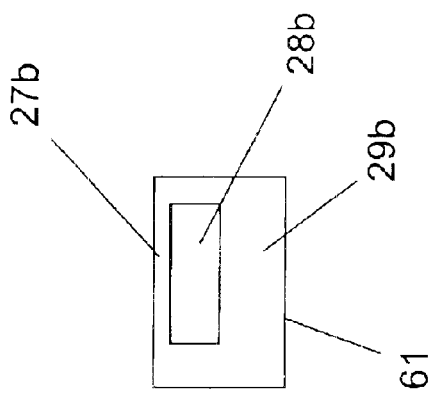
FIG. 2B shows a cross-sectional view of the system component in FIG. 2A.

FIG. 2A shows a plan view of a system component containing a plurality of emitters. In the exemplary embodiment shown in FIG. 2A, the system component is a ring 61. The ring 61 can, for example, be a focus ring, an insulator ring, or a shield ring. Emitters 28a–28d, capable of emitting fluorescent light when exposed to a plasma, are integrated into the ring 61. The number of emitters shown in FIG. 2A is exemplary; any number of emitters can be utilized. The emitters 28a–28d can contain at least one fluorescent material. The emitters can contain different fluorescent materials, or alternatively, the emitters can contain the same fluorescent material(s). Although the emitters 28a–28d are shown as squares in the embodiment in FIG. 2A, this is not required for the invention. In alternate embodiments, the emitters can have different shapes including non-geometrical and/or geometrical shapes, such as rectangular, circular, elliptical, and triangular shapes. FIG. 2B shows a cross-sectional view of the system component in FIG. 2A. Although the cross-sectional shape of emitter 28b is shown as a rectangle in the embodiment in FIG. 2B, this is not required for the invention. In alternate embodiments, the emitter's cross-section can have different shapes including non-geometrical and/or geometrical shapes (e.g., as discussed with respect to FIG. 2A). The emitter 28b can be fully encapsulated by the ring material (e.g., quartz, alumina, or silicon) such that the cover portion 27b over the emitter 28b is made of the same material as the rest of the surrounding material 29b of the ring. Alternatively, the emitter 28b can be partially encapsulated within the surrounding material 29b but covered by a cover portion 27b of a different material. As such, the cover portion can be made of either transparent material or an opaque material. The cover portion 27b can even be made of a filtering material such that a limited number of wavelengths are passed to and from the emitter 28b.

Figure 2D:
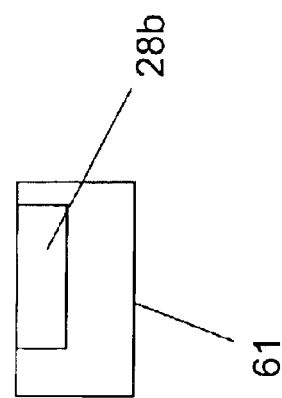
FIG. 2D shows a cross-sectional view of the system component in FIG. 2C.
Figure 2C:
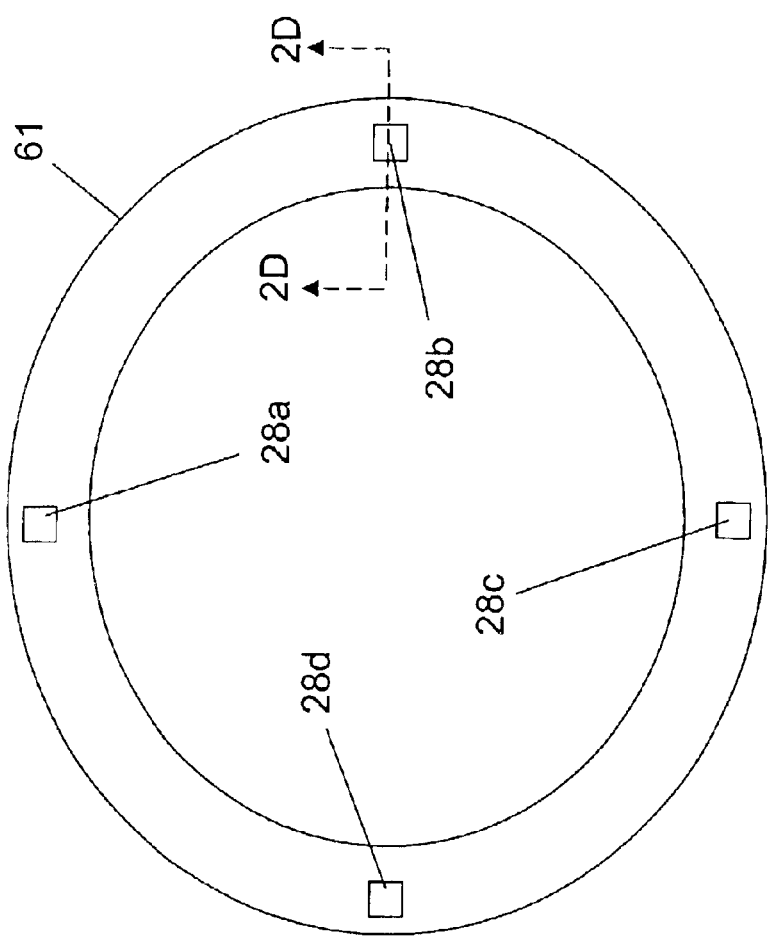
FIG. 2C shows a plan view of an eroded system component containing a plurality of emitters.

FIG. 2C shows a plan view of an eroded system component containing a plurality of emitters. Exposure of the ring 61 in FIG. 2A to a plasma, can result in erosion of the ring 61 and direct exposure of one or more of the emitters 28a–28d to the plasma. Optical monitoring of the process space 12, and the onset of or significant increase in characteristic fluorescent light emission from at least one of emitters 28a–28c, can be utilized to determine whether the system component needs to be replaced. FIG. 2D shows a cross-sectional view of the system component in FIG. 2C.

Alternatively, emitters can be integrated into system components so that the emitters are partially encapsulated by system component material (e.g., quartz, alumina, or silicon). FIG. 3A shows a plan view of system component containing a plurality of emitters. In the embodiment shown in FIG. 3A, the system component is a ring 61. Emitters 28a–28d, can be integrated into a surface of the ring 61 that is exposed to a plasma. FIG. 3B shows a cross-sectional view of the system component in FIG. 3A.

Figure 3D:
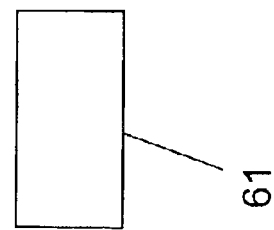
FIG. 3D shows a cross-sectional view of the system component in FIG. 3C.
Figure 3C:
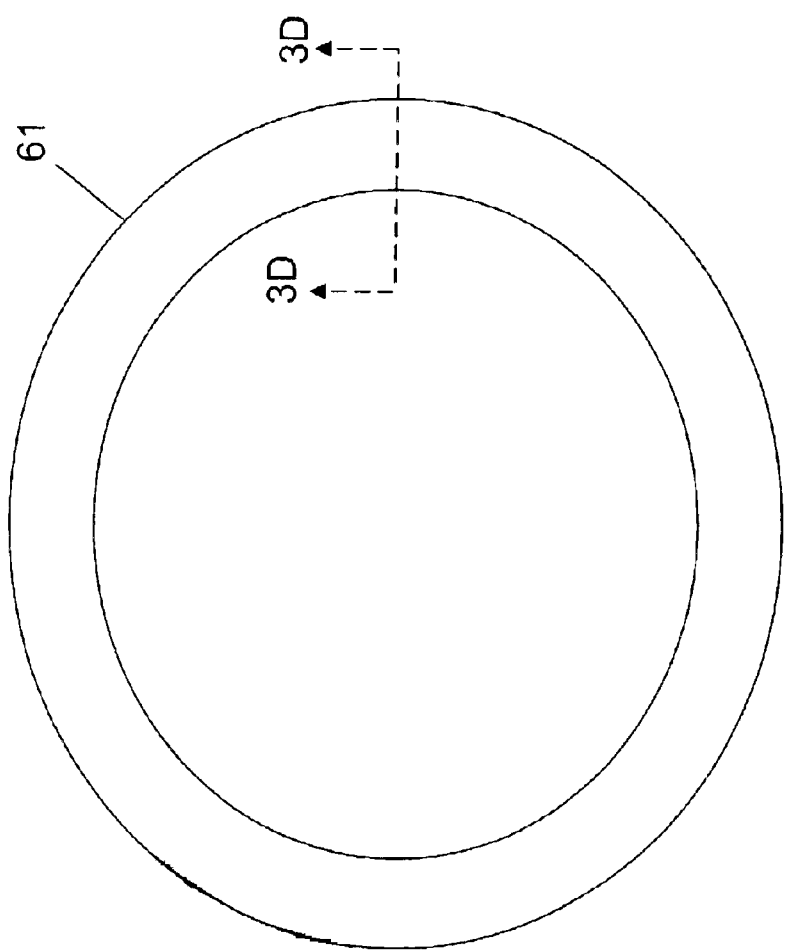
FIG. 3C shows a plan view of an eroded system component.

FIG. 3C shows a plan view of an eroded system component. Exposure of the ring 61 in FIG. 3A to a plasma, can result in erosion of the ring 61 and one or more of the emitters 28a–28d. Optical monitoring of the plasma processing system, and the disappearance of or significant decrease in the characteristic fluorescent light emission can be utilized to determine whether the system component needs to be replaced. FIG. 3D shows a cross-sectional view of the system component in FIG. 3C.

FIG. 4A shows a plan view of a system component containing an emitter. In the embodiment shown in FIG. 4A, the system component is a ring 61 (having various subsections 75) that encircles substrate 35. The emitter 28 is ring shaped and fully encapsulated by the ring material. Alternatively, the emitter can be partially encapsulated by the ring material. FIG. 4B shows a cross-sectional view of the system component in FIG. 4A. The emitter 28 is fully encapsulated by the ring material. Alternatively, the emitter 28 can be partially encapsulated by the ring material and partially exposed to the plasma. Each subsection 75 may be made of one or more fluorescent materials. Moreover, the one or more materials may change from subsection-to-subsection, or may be constant across all subsections 75. Although depicted as containing 8 subsections 75, the number of subsections may be varied to provide varying amounts of spatial resolution of the erosion of the ring 61.

Figure 5A:
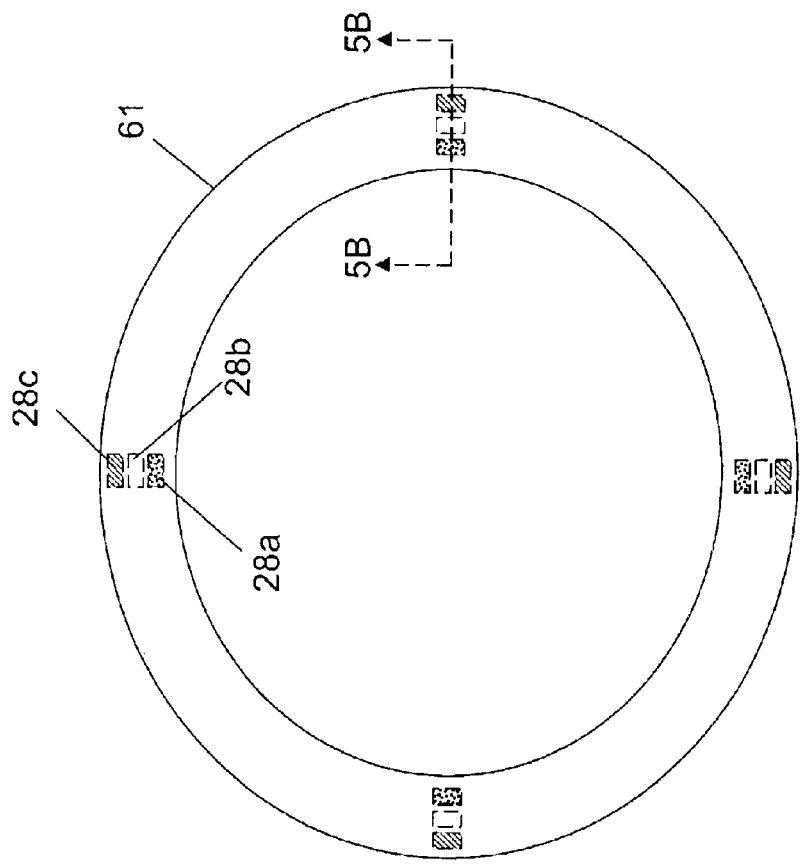
FIG. 5A shows a plan view of a system component containing a plurality of emitters.
Figure 5B:
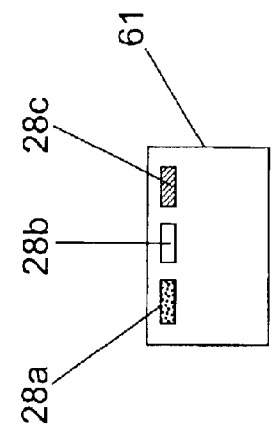
FIG. 5B shows a cross-sectional view of the system component in FIG. 5A.

FIG. 5A shows a plan view of a system component containing a plurality of emitters. In the embodiment shown in FIG. 5A, the system component is a ring 61. Emitters 28a–28c, capable of emitting fluorescent light when exposed to a plasma, are integrated into the ring 61 at different radial positions and are fully encapsulated by the ring material. Alternatively, the emitters can be integrated into the ring 61 at the same radial positions. Alternatively, the emitters can be partially encapsulated by the ring material. The number of emitters shown in FIG. 5A is exemplary; any number of emitters can be utilized. The emitters 28a–28c can contain at least one fluorescent material. The emitters can contain different fluorescent materials, or alternatively, the emitters can contain the same fluorescent material(s). By using one set of materials at one location (e.g., at zero degrees on the unit circle) and by using a different set of materials at other locations (e.g., at 90, 180 and 270 degrees on the unit circle), the optical emissions of the ring 61 can be spatially resolved. FIG. 5B shows a cross-sectional view of the system component in FIG. 5A.

Figure 5C:
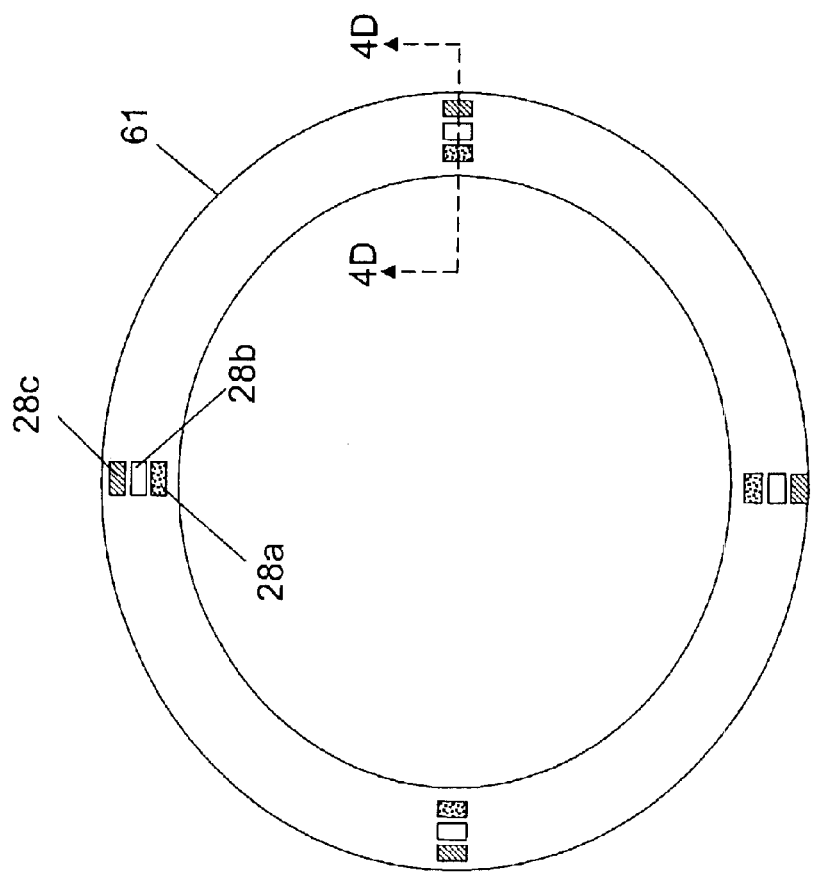
FIG. 5C shows a plan view of an eroded system component.
Figure 5D:
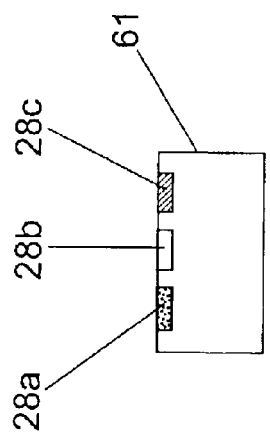
FIG. 5D shows a cross-sectional view of the system component in FIG. 5C.

FIG. 5C shows a plan view of an eroded system component. Exposure of the ring 61 in FIG. 5C to a plasma, can result in erosion of the ring 61 and direct exposure of one or more of the emitters 28a–28c to the plasma. Optical monitoring of the plasma processing system, and the onset of or significant increase in characteristic fluorescent light emission can be utilized to determine whether the system component needs to be replaced. FIG. 5D shows a cross-sectional view of the system component in FIG. 5C. If the ring 61 erodes uniformly, fluorescent light emission from exposed emitters 28a–28c can appear substantially at the same time. However, if the ring 61 etches non-uniformly (not shown) during plasma processing, the characteristic fluorescent light emission from one or more of emitters 28a–28c can provide spatial erosion information, in addition to the extent of the erosion.

Figure 6A:
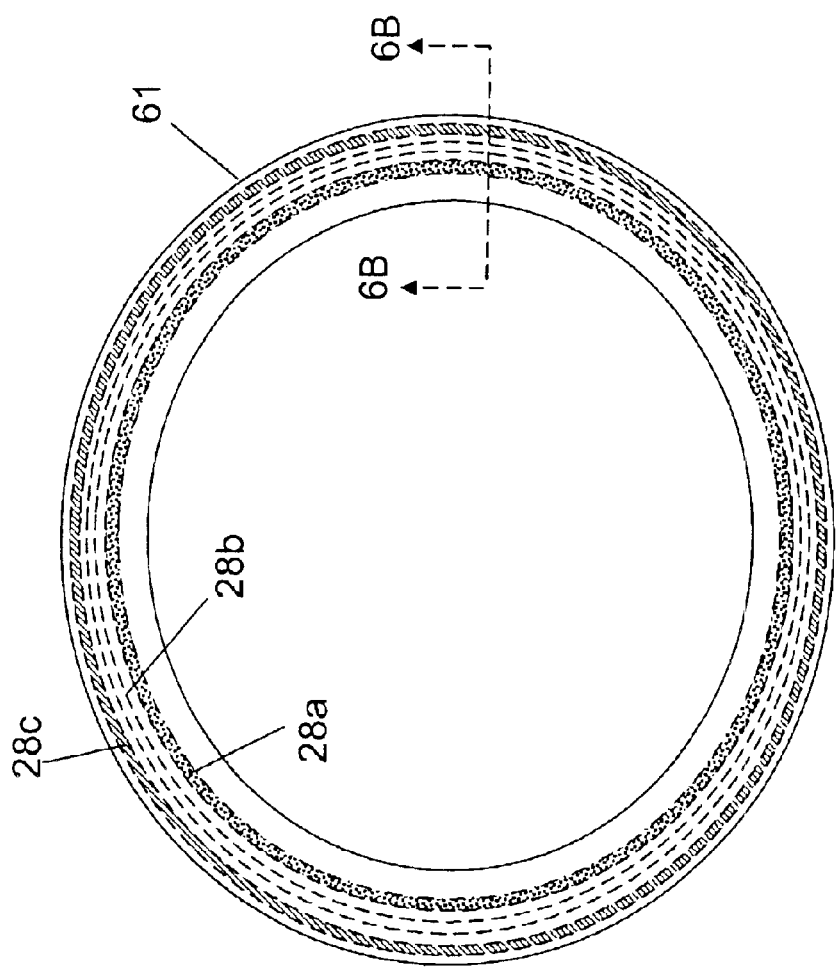
FIG. 6A shows a plan view of a system component containing a plurality of emitters.
Figure 6B:
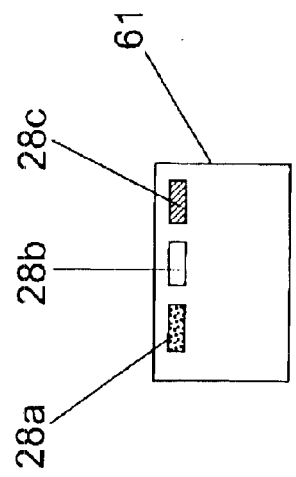
FIG. 6B shows a cross-sectional view of the system component in FIG. 6A.

FIG. 6A shows a plan view of a system component containing a plurality of emitters. In the embodiment shown in FIG. 6A, the system component is a ring 61. Emitters 28a–28c, capable of emitting fluorescent light when exposed to a plasma, are integrated into the ring 61 as concentric rings at different radial positions and are fully encapsulated by the ring material. Alternatively, the emitters can be partially encapsulated by ring material or not encapsulated. The number of emitters shown in FIG. 6A is exemplary; any number of emitters can be utilized. The emitters 28a–28c can contain at least one fluorescent material. The emitters can contain different fluorescent materials, or alternatively, the emitters can contain the same fluorescent material(s). FIG. 6B shows a cross-sectional view of the system component in FIG. 6A. Spatial distribution of emitters 28a, 28b, and 28c can be used to measure non-uniform erosion of the system component.

Figure 7A:
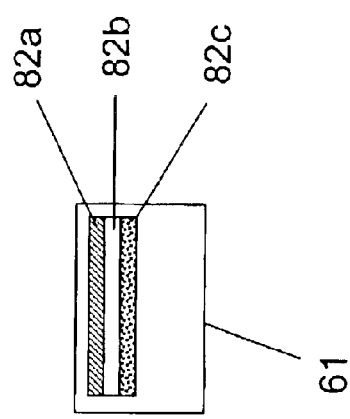
FIG. 7A shows a cross-sectional view of a system component containing a plurality of emitters.

FIG. 7A shows a cross-sectional view of a system component containing a emitter stack including layers 82a–82c. In the embodiment shown in FIG. 7A, the system component is a ring 61. In a first embodiment of the stack, the layers 82a–82c are each a different type of fluorescent material such that the erosion of each layer is signaled by a change to a new emission type. In a second embodiment, the first layer 82a is an opaque layer that initially blocks transmission of light to the third layer 82c which is made of a fluorescent material. In the second embodiment, the second layer 82b can be either a (substantially) transparent layer or a filter. If the second layer 82b reduces the amount of emission by the third layer 82c, then the erosion of the second layer 82b will be signaled by an increasing amount of emission from the third layer 82c.

Figure 7B:
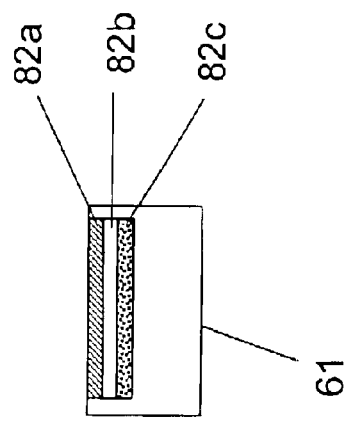
FIG. 7B shows a cross-sectional view of an eroded system component containing a plurality of emitters.

FIG. 7B shows a cross-sectional view of an eroded system component containing an emitter stack. Exposure of the ring 61 in FIG. 7A to a plasma, can result in erosion of the ring 61 and direct exposure of layer 82a to the plasma. In the first embodiment described above, optical monitoring of the plasma processing system, and the onset of or significant increase in characteristic fluorescent light emission from the layer 82a can be utilized to determine the status of the ring. In addition, disappearance of a characteristic fluorescent light emission from an emitter can be used to determine the status of the ring.

Figure 7C:
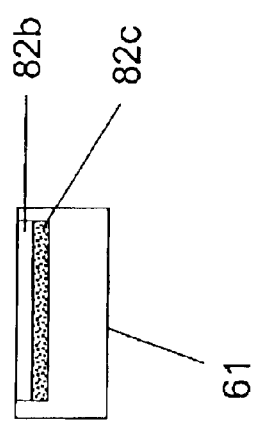
FIG. 7C shows a cross-sectional view of an eroded system component containing a plurality of emitters.

FIG. 7C shows a cross-sectional view of an eroded system component containing an emitter stack. Further exposure of the ring 61 in FIG. 7B to a plasma, can result in direct exposure of layer 82b to the plasma. Optical monitoring of the plasma processing system, and the onset of or significant increase in characteristic fluorescent light emission from layer 82b (in the first embodiment) or layer 82c (in the second embodiment) can be utilized to determine the status of the ring.

Figure 8B:
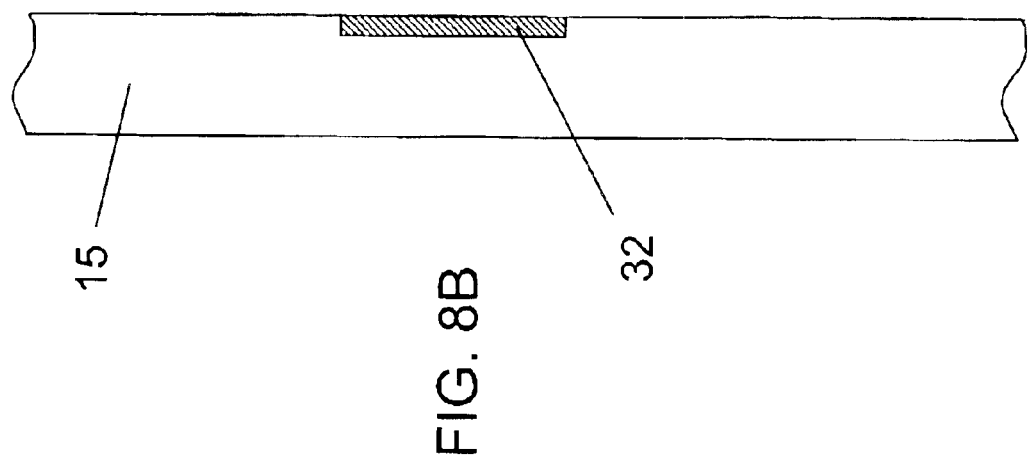
FIG. 8B shows a cross-sectional view of an eroded system component containing an emitter.
Figure 8A:
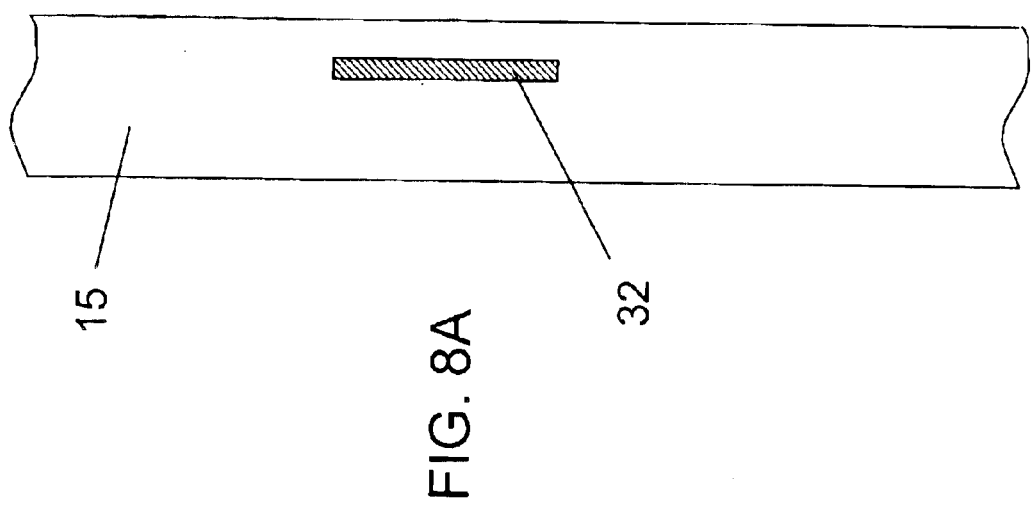
FIG. 8A shows a cross-sectional view of a system component containing an emitter.

FIG. 8A shows a cross-sectional view of a system component containing an emitter. In the embodiment shown in FIG. 8A, the system component 15 can, for example, be a ring, a shield, an electrode, a baffle, or a liner. In one embodiment the system component 15 is shield that reduces erosion of chamber walls during plasma processing. An emitter 32, containing at least one fluorescent material and capable of emitting fluorescent light when exposed to a plasma, is integrated into the system component 15. The emitter 32 is fully encapsulated by the ring material (e.g., quartz or alumina). Alternatively, the emitter can be partially encapsulated by ring material.

FIG. 8B shows a cross-sectional view of an eroded system component containing an emitter. During plasma processing, the system component 15 can be exposed to the plasma environment and this can result in erosion of the system component 15, and direct exposure of the emitter 32 to the plasma environment. Optical monitoring of the plasma processing system, and the onset of or significant increase in characteristic fluorescent light emission from emitter 32, can be utilized to determine whether the system component needs to be replaced. Alternatively, if the system component 15 is fabricated to partially encapsulate the emitter by system component material, the disappearance of or significant decrease in characteristic fluorescent light emission from emitter 32 can be utilized to determine the status of the system component 15, and if the system component 15 needs to be replaced.

Figure 9C:
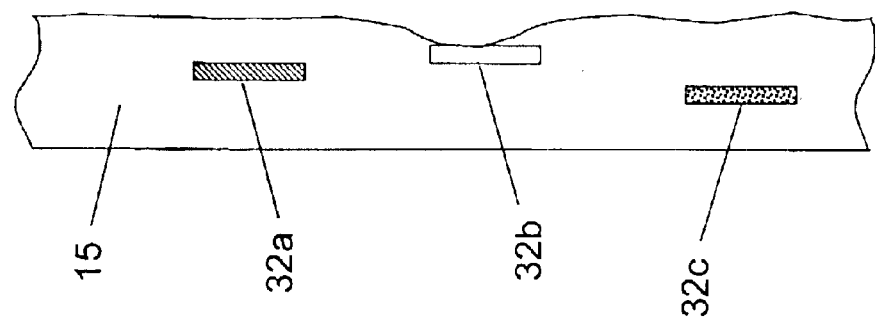
FIG. 9C shows a cross-sectional view of an eroded system component containing a plurality of emitters.
Figure 9B:
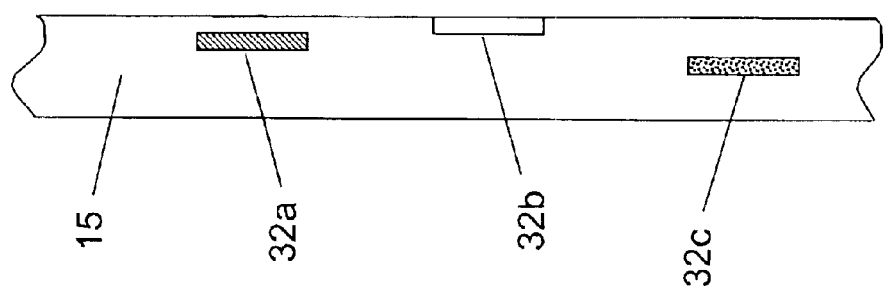
FIG. 9B shows a cross-sectional view of an eroded system component containing a plurality of emitters.
Figure 9A:
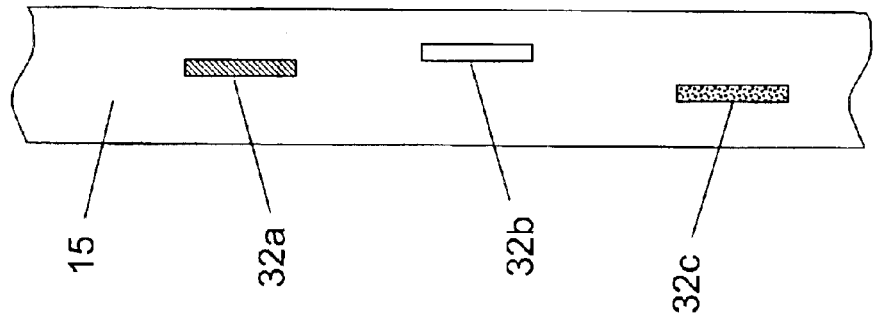
FIG. 9A shows a cross-sectional view of a system component containing a plurality of emitters.

FIG. 9A shows a cross-sectional view of a system component containing a plurality of emitters. In the embodiment shown in FIG. 9A, the system component 15 contains emitters 32a–32c that are fully encapsulated by the system component material. Alternatively, the emitters can be partially encapsulated by system component material. While illustrated as being embedded at different depths, the emitters 32a–32c could be embedded at the same depth. As would be appreciated, the depth of each emitter to be buried within the surface may be determined empirically by examining eroded surfaces and when such erosion decreased system performance or cleanliness.

FIG. 9B shows a cross-sectional view of an eroded system component containing a plurality of emitters. The system component 15 is uniformly eroded, and fluorescent signals from emitters 32a–32c can appear substantially at the same time. FIG. 9C shows a cross-sectional view of an eroded system component containing a plurality of emitters. If the system component 15 etches non-uniformly during plasma processing, the characteristic fluorescent light emission from one or more of emitters 32a–32c can provide spatial erosion information, in addition to information on the extent of the erosion.

In alternate embodiments, fluorescent emitters can be integrated into system components by depositing a protective barrier on the surfaces of system components containing at least one emitter. The role of a protective barrier can be to reduce erosion of the system components during plasma processing. A protective barrier can be substantially transparent to plasma light over a wide range of wavelengths. A protective barrier comprising, for example Yttria ($Y_2O_3$), can be formed using (thermal) spray coating techniques that are well known to those skilled in the art of ceramic spray coatings. In an alternate embodiment, forming the protective barrier can further comprise polishing the thermal spray coating. For example, polishing the thermal spray coating can comprise the application of sand paper to the sprayed surfaces. The protective barrier can comprise at least one of $Y_2O_3$, $Sc_2O_3$, $Sc_2F_3$, $YF_3$, $La_2O_3$, $CeO_2$, $Eu_2O_3$, $DyO_3$, $SiO_2$, MgO, $Al_2O_3$, ZnO, $SnO_2$, and $In_2O_3$, The protective barrier thickness can range from 0.5 microns to 500 microns, for example. Alternatively, the protective barrier can comprise a phosphor material, e.g. $Y_2O_3$:Eu. Disappearance of a characteristic fluorescent light emission from a phosphor material in a protective barrier can be used to determine the status of a system component.

Figure 10:
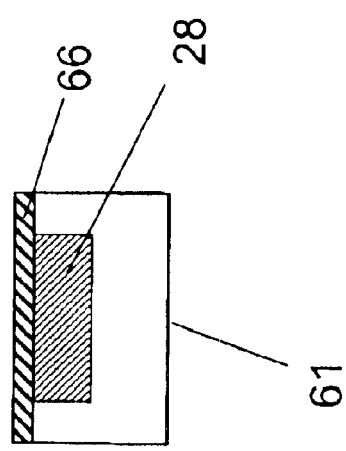
FIG. 10 shows a cross-sectional view of a system component containing an emitter and a protective layer.

FIG. 10 shows a cross-sectional view of a system component containing an emitter. In FIG. 10, the system component is a ring 61. The ring 61 can, for example, be a focus ring, an insulator ring, or a shield ring. A protective barrier layer 66 is deposited on the emitter 28 and system component 61 to reduce erosion. Changes in the fluorescent emissions from emitter 28 during plasma processing can indicate erosion of the protective barrier layer 66.

Figure 11:
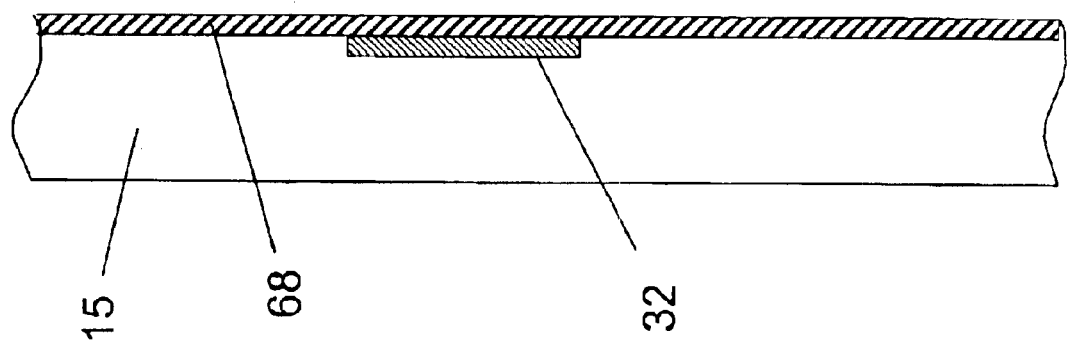
FIG. 11 shows a cross-sectional view of a system component containing an emitter and a protective layer.

FIG. 11 shows a cross-sectional view of a system component containing an emitter. In the embodiment shown in FIG. 11, the system component 15 can, for example, be a ring, a shield, an electrode, a baffle, or a liner. A protective barrier layer 68 is deposited on the emitter 32 and system component 15 to reduce erosion. Fluorescent emission from emitter 32 during plasma processing can indicate erosion of the protective barrier layer 68.

The status of a system component can be determined during plasma processing, by monitoring the characteristic fluorescent emission from an emitter integrated into the system component. One possible method for determining the status of a system component is to use optical emission spectroscopy (OES) to monitor a wavelength range where the characteristic fluorescent emission occurs. A system component can contain at least one emitter, that is capable of fluorescent emission at characteristic wavelength(s), that allows for identification of the system component. When an intensity level of an emission with a characteristic wavelength crosses a specified threshold value (e.g., increase above a particular value or drop to substantially zero), a determination can be made whether the system component needs to be replaced, and based on the determination, the process can be continued or stopped.

FIG. 12 is a flowchart for monitoring the status of system components using optical emission. In step 100, the process is started. In step 102, an optical signal from the plasma processing region is monitored using an optical monitoring system. In step 104, the optical signal is analyzed for characteristic light emission from an emitter integrated into a system component. If the characteristic light emission from an emitter exceeds a threshold value, a determination is made in step 106 on whether to continue the process or to stop the process in step 108.

Determining whether the process should be continued in step 106 can depend on the fluorescent emission that is detected, e.g., identifying the system component. Furthermore, fluorescent emission from a plurality of emitters integrated into a system component can indicate if the system component is eroding uniformly during plasma processing and can therefore provide spatial erosion information, in addition to the extent of the erosion.

This method of monitoring the status of system components using emitters, provides a new in-situ method for monitoring erosion of system components in a plasma environment. The consumption of consumable system components can be monitored during plasma processing, without the need for disassembly of the plasma processing system. The method can significantly reduce the risk of overdue or premature replacement of consumable components, and avoid processing conditions that are outside process specifications due to erosion of system components.

It should be understood that various modifications and variations of the present invention may be employed in practicing the invention. It is therefore to be understood that, within the scope of the appended claims, the invention may be practiced otherwise than as specifically described herein.

What is claimed is:

1. A method of monitoring erosion of a system component in a plasma processing system, the method comprising:
exposing a system component to a plasma, the system component containing an emitter capable of fluorescent light emission when excited by light from the plasma; and
monitoring the fluorescent light emission from the plasma processing system during a process to determine erosion of the system component.

2. The method according to claim 1, wherein the fluorescent light emission relates to an amount of erosion of the system component.

3. The method according to claim 1, wherein the system component comprises a consumable part.

4. The method according to claim 1, wherein the system component comprises at least one of a ring, a shield, an electrode, a baffle, and a liner.

5. The method according to claim 1, wherein the emitter comprises at least one material having fluorescent properties when excited by excited gas species produced in the plasma.

6. The method according to claim 1, wherein the monitoring comprises using an optical monitoring system to detect the fluorescent light emission.

7. The method according to claim 6, wherein the monitoring further comprises determining if the intensity level of the fluorescent emission exceeds a threshold value.

8. The method according to claim 6, wherein the monitoring further comprises identifying the system component from the wavelength of the fluorescent light emission.

9. The method according to claim 6, wherein the monitoring further comprises measuring an intensity level of the fluorescent emission to arrive at a determination of whether the component needs to be replaced, and based on the determination, either continuing with the process or stopping the process.

10. A method of monitoring system component status in a plasma processing system, the method comprising:
exposing a system component to a plasma, the system component containing an emitter capable of fluorescent light emission when excited by light from the plasma; and
monitoring fluorescent light emission from the plasma processing system during a process, the monitoring including using an optical monitoring system to detect the wavelength and the intensity level of the fluorescent light emission, identifying the system component from the wavelength of the fluorescent light emission, and arriving at a determination of erosion level of the system component.

11. A plasma processing system, comprising:
a plasma processing chamber;
a plasma source configured to create a plasma from a process gas;
a system component containing an emitter capable of fluorescent light emission when excited by light from a plasma;
an optical monitoring system for monitoring light emission from the plasma processing chamber during processing to monitor erosion level of the system component; and
a controller configured to control the plasma processing system.

12. The system according to claim 11, wherein the system component comprises a consumable part.

13. The system according to claim 11, wherein the system component comprises at least one of a ring, a shield, an electrode, a baffle, and a liner.

14. The system according to claim 11 wherein the system component is fabricated from least one of silicon, quartz, alumina, carbon, silicon carbide, aluminum, and stainless steel.

15. The system according to claim 11, wherein the emitter comprises at least one material having fluorescent properties when excited by excited gas species produced in the plasma.

16. The system according to claim 15, wherein the at least one material comprises a phosphor material.

17. The system according to claim 11, wherein the emitter comprises at least one of $Y_2O_3$:Eu, $Y_2O_2$S:Eu, $Y_2O_2$S:Tb, $Y_2O_2$S:EuTb, ZnS:Cu, ZnS:Al, ZnS:CuAl, $SrGa_2S_4$:Ce, ZnS:Ag, ZnS:Au, ZnS:Cl, ZnS:AgAu, ZnS:AgCl, ZnS:AuCl, ZnS:AgAuCl, and $SrGa_2S_4$:Ce.

18. The system according to claim 11, wherein the system component further comprises a protective barrier.

19. The system according to claim 11, wherein the protective barrier comprises at least one of $Y_2O_3$, $Sc_2O_3$, $Sc_2F_3$, $YF_3$, $La_2O_3$, $CeO_2$, $Eu_2O_3$, $DyO_3$, $SiO_2$, MgO, $Al_2O_3$, ZnO, $SnO_2$, and $In_2O_3$.

20. The system according to claim 18, wherein the protective barrier is transparent.

21. The system according to claim 11, wherein the plasma source comprises an inductive coil.

22. The system according to claim 11, wherein the plasma source comprises a plate electrode.

23. The system according to claim 11, wherein the plasma source comprises an ECR source.

24. The system according to claim 11, wherein the plasma source comprises a Helicon wave source.

25. The system according to claim 11, wherein the plasma source comprises a surface wave source.

26. A plasma processing system, comprising:
a plasma processing chamber;
a plasma source configured to create a plasma from a process gas;

a system component containing an emitter capable of fluorescent light emission when excited by light from a plasma;

an optical monitoring system for monitoring light emission from the plasma processing chamber during processing to monitor erosion level of the system component; wherein the optical monitoring system is further configured to identify the system component from the wavelength of the fluorescent light emission, to determine if the intensity level of the fluorescent emission exceeds a threshold value, to determine if the system component needs to be replaced, and based on the determination, either continue with the process or stop the process; and a controller configured to control the plasma processing system.

27. A monitorable consumable system component, comprising:

a component element; and an emitter coupled to the component element, the emitter being capable of fluorescent light emission when excited by light from a plasma, wherein the light emission is used to monitor erosion level of the system component.

28. The consumable system component according to claim 27, wherein the component element comprises a ring, a shield, an electrode, a baffle, or a liner.

29. The consumable system component according to claim 27, wherein the component element is a focus ring.

30. The consumable system component according to claim 27, wherein the component element is an electrode plate.

31. The consumable system component according to claim 27, wherein the component element is a deposition shield.

32. The consumable system component according to claim 27, wherein the component element is fabricated from least one of silicon, quartz, alumina, carbon, silicon carbide, aluminum, and stainless steel.

33. The consumable system component according to claim 27, wherein the emitter is fully encapsulated by the component element.

34. The consumable system component according to claim 27, wherein the emitter is partially encapsulated by the component element.

35. The consumable system component according to claim 27, wherein the emitter comprises at least one material having fluorescent properties when excited by excited gas species produced in a plasma.

36. The consumable system component according to claim 27, wherein the light emission from the emitter allows for identifying the consumable system component.

37. The consumable system component according to claim 27, wherein the emitter comprises a phosphor material.

38. The consumable system component according to claim 27, wherein the emitter comprises at least one of $Y_2O_3$:Eu, $Y_2O_2$S:Eu, $Y_2O_2$S:Tb, $Y_2O_2$S:EuTb, ZnS:Cu, ZnS:Al, ZnS:CuAl, $SrGa_2S_4$:Ce, ZnS:Ag, ZnS:Au, ZnS:Cl, ZnS:AgAu, ZnS:AgCl, ZnS:AuCl, ZnS:AgAuCl, and $SrGa_2S_4$:Ce.

39. The consumable system component according to claim 27, wherein the system component further comprises a protective barrier.

40. The consumable system component according to claim 39 wherein the protective barrier comprises at least one of $Y_2O_3$, $Sc_2O_3$, $Sc_2F_3$, $YF_3$, $La_2O_3$, $CeO_2$, $Eu_2O_3$, $DyO_3$, $SiO_2$, MgO, $Al_2O_3$, ZnO, $SnO_2$, and $In_2O_3$.

41. The consumable system component according to claim 39 wherein the protective barrier comprises at least one material having fluorescent properties when excited by light produced in a plasma.

42. The consumable system component according to claim 39 wherein the protective barrier comprises at least one material having fluorescent properties when excited by excited gas species produced in a plasma.

43. The consumable system component according to claim 39 wherein the protective barrier is transparent.

* * * * *